United States Patent [19]

Bajnógel et al.

[11] Patent Number: 5,523,303
[45] Date of Patent: Jun. 4, 1996

[54] TRISUBSTITUTED CYCLOALKANE DERIVATIVES AND PROCESS FOR THE PREPARATION THEREOF

[75] Inventors: Judit Bajnógel; Gábor Blaskó; Zoltán Budai; András Egyed; Márton Fekete; Erika Karaffa; Tibor Mezei; Klára Reiter née Esses; Gyula Simig; Katalin Szemerédi; Enikö Szirt née Kiszelly, all of Budapest, Hungary

[73] Assignee: Egis Gyogyszergyar Rt., Budapest, Hungary

[21] Appl. No.: 226,051

[22] Filed: Apr. 11, 1994

[30] Foreign Application Priority Data

Apr. 9, 1993 [HU] Hungary ................................. 1041/93

[51] Int. Cl.[6] .................... A61K 31/15; A61K 31/495
[52] U.S. Cl. .................... 514/255; 514/238.2; 514/331; 514/428; 514/640; 514/925; 514/926; 514/927; 514/928; 544/165; 544/398; 546/223; 548/569
[58] Field of Search .................... 514/925, 926, 514/927, 928, 640, 238.2, 255, 331, 428; 564/256; 544/165, 398; 546/223; 548/569

[56] References Cited

U.S. PATENT DOCUMENTS

| | | | |
|---|---|---|---|
| 4,077,999 | 3/1978 | Budai et al. | 260/566 |
| 4,477,453 | 10/1984 | Astoin et al. | 424/250 |
| 4,727,074 | 2/1988 | Budai et al. | 514/255 |
| 5,130,487 | 7/1992 | Budai et al. | 564/256 |

OTHER PUBLICATIONS

Astoin et al; *Chem Abst.* 99:175381 (1983).

*Primary Examiner*—Peter O'Sullivan
*Attorney, Agent, or Firm*—Beveridge, DeGrandi, Weilacher & Young

[57] ABSTRACT

The invention relates to novel, pharmaceutically active trisubstituted cycloalkane derivatives, a process for the preparation thereof and pharmaceutical compositions comprising the same. The invention also encompasses the use of the said cycloalkane derivatives for the treatment of diseases and for the preparation of pharmaceutical compositions suitable for the treatment of diseases.

The compounds according to the invention are characterized by the general formula (I),

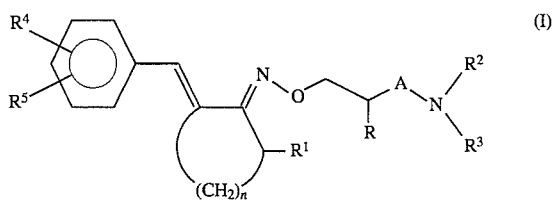

wherein R represents hydrogen, $C_{1-4}$ alkyl or hydroxyl, $R^1$ stands for $C_{1-12}$ alkyl, $R^2$ and $R^3$ each represents hydrogen, $C_{1-12}$ alkyl or $C_{2-12}$ alkenyl, or $R^2$ and $R^3$ together with the adjacent nitrogen atom form a 4- to 7-membered ring optionally comprising an oxygen, sulfur or a further nitrogen atom, which latter may carry a phenyl, benzyl or $C_{1-4}$ alkyl substituent, $R^4$ and $R^5$ each stands for hydrogen, halogen or $C_{1-4}$ alkoxy, or together represent a 3,4-methylenedioxy group, n is an integer from 2 to 5, A represents a valency bond or a —$CH_2$— group.

The compounds exert a valuable antiulcer effect, so they can be used to advantage in the therapy.

4 Claims, No Drawings

TRISUBSTITUTED CYCLOALKANE DERIVATIVES AND PROCESS FOR THE PREPARATION THEREOF

The present invention relates to novel, pharmaceutically active trisubstituted cycloalkane derivatives, a process for the preparation thereof, pharmaceutical compositions comprising the same, to the use of the said cycloalkane derivatives for the treatment of diseases and for the preparation of pharmaceutical compositions suitable for the treatment of diseases.

According to an aspect of the present invention there are provided new trisubstituted cycloalkane derivatives of general formula (I),

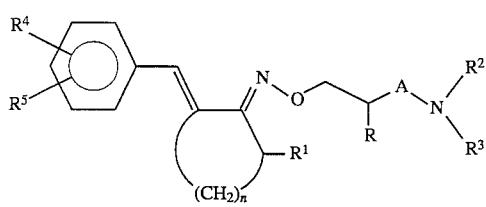

wherein

R represents hydrogen, $C_{1-4}$ alkyl or hydroxyl, $R^1$ stands for $C_{1-12}$ alkyl, $R^2$ and $R^3$ each represents hydrogen, $C_{1-12}$ alkyl or $C_{2-12}$ alkenyl, or $R^2$ and $R^3$ together with the adjacent nitrogen atom form a 4- to 7-membered ring optionally comprising an oxygen, sulfur or a further nitrogen atom, which latter may carry a phenyl, benzyl or $C_{1-4}$ alkyl substituent, $R^4$ and $R^5$ each stands for hydrogen, halogen or $C_{1-4}$ alkoxy, or together represent a 3,4-methylenedioxy group, n is an integer from 2 to 5, A represents a valency bond or a —$CH_2$— group, stereo and optically active isomers and their possible mixtures, acid-addition salts and quaternary ammonium derivatives thereof.

The term "alkyl group" used throughout the specification relates to straight or branched chained saturated aliphatic hydrocarbon groups having the given number of carbon atom(s), e.g. methyl, ethyl, propyl, isopropyl, n-butyl, tert-butyl etc. The term "alkenyl group" relates to straight or branched chained alkenyl groups containing the given number of carbon atoms, e.g. vinyl, allyl, 2-methyl-allyl, 1-propenyl, 1-butenyl, 2-butenyl, 2-hexenyl etc. The term "alkoxy group" relates to alkyl ether groups comprising 1 to 4 carbon atom(s), e.g. methoxy, ethoxy, tert-butoxy etc. The term "halogen atom" encompasses all the four halogen atoms (fluorine, chlorine, bromine and iodine). As "4- to 7-membered ring" aromatic or partially or completely saturated heterocyclic rings are mentioned, which contain as heteroatom a nitrogen and optionally an oxygen, sulfur or further nitrogen atom (e.g. piperidyl, morpholinyl, piperazinyl, furyl, imidazolyl, pyridinyl, pyrazolyl, imidazolyl etc.), and the latter heteroatom may optionally carry a phenyl, benzyl or $C_{1-4}$ alkyl substituent. In the preferred representatives of the compounds of the general formula (I) $R^1$ stands for $C_{1-8}$ alkyl, $R^2$ and $R^3$ each represents $C_{1-4}$ alkyl or together with the adjacent nitrogen atom form a 5- or 6-membered ring optionally comprising a further nitrogen atom, which latter may carry a benzyl substituent, $R^4$ and $R^5$ each stands for hydrogen, halogen or methoxy, n is 3 or 4 and A and R are as stated above.

Particularly preferred representatives of the compounds of general formula (I) are the following derivatives:

(R,S)-6-(E)-(4-fluorophenylmethylene)-2-pentyl-1-(E)-[2-(phenylmethyl-1-piperazinyl)-ethoxyimino]-cyclohexane, (R,S)-2-propyl-7-(E)-(4-chlorophenylmethylene)-1-(E)-[2-hydroxy-3-(N-pyrrolidinylpropoxyimino)]-cycloheptane, (R,S)-6-(E)-(4-fluorophenylmethylene)-2-methyl-1-(E)-[3-(dimethylamino)-2-methylpropoxyimino)-cyclohexane, (R,S)-6-(E)-(2-methoxyphenylmethylene)-2-hexyl-1-(E)-[2-(diethylamino)-ethoxyimino]-cyclohexane, (R,S)-6-(E)-(4-fluorophenylmethylene)-2-heptyl-1-(E)-[2-(dimethylamino)-ethoxyimino]-cyclohexane, (R,S)-7-(E)-(4-chlorophenylmethylene)-2-propyl-1-(E)-[2-(diethylamino)-ethoxyimino]-cycloheptane, (R,S)-6-(E)-(3,4-dichlorophenylmethylene)-2-methyl-1-(E)-[2-(diethylamino)-ethoxyimino]-cyclohexane, stereo and optically active isomers, acid-addition salts and quaternary ammonium derivatives thereof.

Some aminohydroxypropoxyimino derivatives are known in the art but their chemical structure and pharmaceutical activity are different from those of the compounds of the present invention.

The fluorene derivative "IPS-339" of formula (VI)

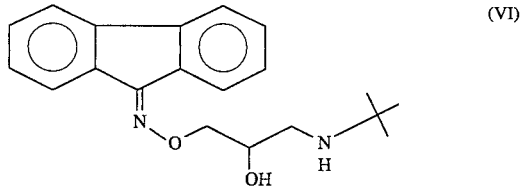

and the methyl cyclopropylketone derivative of formula (VII)

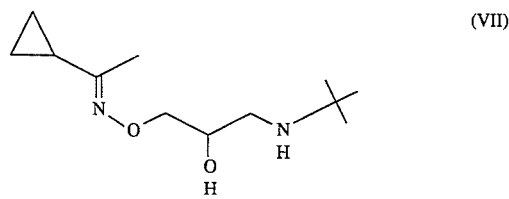

known as Falintolol exhibit beta-adrenergic blocking activity.

The published PCT patent application No. 8,402,908 describes carbostyrylketoxime derivatives possessing beta-adrenergic blocking activity. These compounds are useful in the treatment of glaucoma.

The Belgian patent specification No. 886,471 describes benzothiophene derivatives of general formula (VIII),

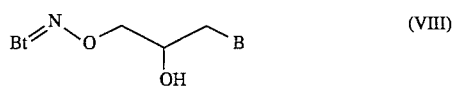

wherein Bt represents a benzothiophene group and B stands for a basis group containing a nitrogen atom.

Peraclopon of formula (IX)

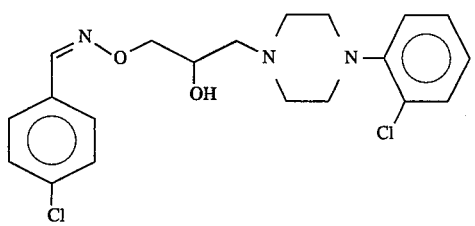

is a lipid level lowering agent, and Peradoxime of the formula (X)

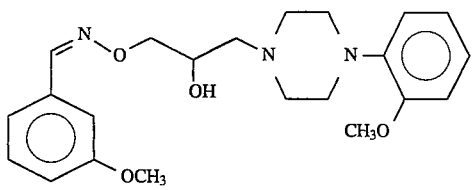

has a hypotensive effect.

The U.S. Pat. No. 4,652,586 relates to compounds of general formula (VIII), wherein Bt is a fluorene group. The compounds reduce the inner pressure of eye and exhibit a selective beta-two-adrenergic antagonist effect.

The published German patent application No. 4,027,052 relates to disubstituted cycloalkane derivatives possessing primarily antiarrhythmic properties and having the following formula (XI),

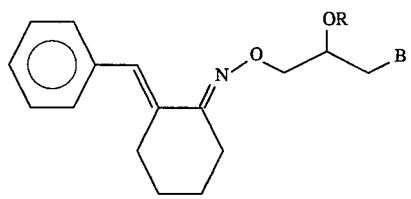

wherein R stands for hydrogen or benzoyl and B is a basic group containing a nitrogen atom.

The European patent specification No. 5,129 describes a new substituted benzimidazole derivative of formula (XII),

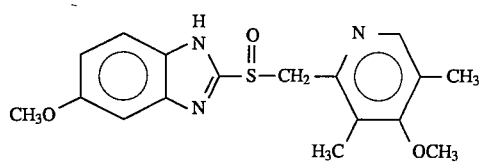

which is the first representative of the compounds having $H^+/K^+$-ATP-ase inhibiting activity.

The Hungarian patent specification No. 194,244 describes compounds of general formula (XIII)

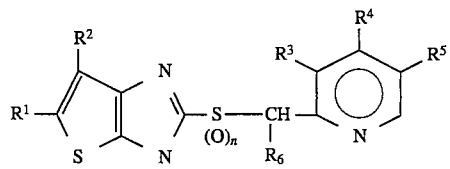

wherein n is 0 or 1, $R^1$, $R^2$ and $R^6$ each represents hydrogen, alkyl or alkoxy and $R^3$, $R^4$ and $R^5$ each stands for halogen, alkyl or alkoxy exerting $H^+/K^+$-ATP-ase inhibiting effect.

The chemical structure of the trisubstituted cyclo-alkane derivatives of general formula (I) according to the invention is basically different from that of the prior art compounds and the activity thereof is surprising.

According to another aspect of the present invention there is provided a process for the preparation of trisubstituted cycloalkane derivatives of general formula (I), stereo and optically active isomers and their possible mixtures, acid-addition salts and quaternary ammonium derivatives thereof, which comprises a) reacting a cycloalkane derivative of general formula (II),

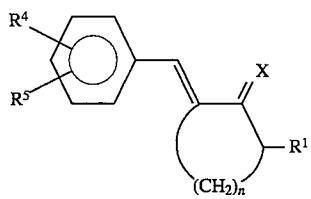

wherein $R^1$, $R^4$, $R^5$ and n are as stated above and X stands for oxygen or sulfur, with a substituted alkane of general formula (III),

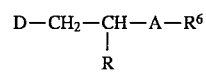

wherein D represents a group of formula $H_2N-O-$, $R^6$ stands for a group of formula $-NR^2R^3$, R and A are as stated above, or in the presence of a basic condensing agent with the acid addition salt thereof; or b) for the preparation of compounds of general formula (I), wherein R represents hydrogen or $C_{1-4}$ alkyl, reacting a cycloalkane derivative of general formula (II), wherein $R^1$, $R^4$, $R^5$ and n are as stated above and X stands for a group of formula $=N-OH$, with a substituted alkane of general formula (III), wherein D stands for halogen, R represents hydrogen or $C_{1-4}$ alkyl, $R^6$ is a group of formula $-NR^2R^3$ and A is as stated above, in the presence of a basic condensing agent, or c) for the preparation of compounds of general formula (I), wherein R represents hydroxy, A stands for a group of formula $-CH_2-$, $R^1$, $R^2$, $R^3$, $R^4$, $R^5$ and n are as stated above, reacting a cycloalkane derivative of general formula (II), wherein X represents a group of formula $=N-OH$, $R^1$, $R^4$, $R^5$ and n are as stated above, with a halo compound of general formula (III), wherein D represents halogen, A, $R^6$ and R together stand for a group of formula $-CH_2-O-$, in the presence of a basic condensing agent, and reacting the epoxy compound of general formula (V)

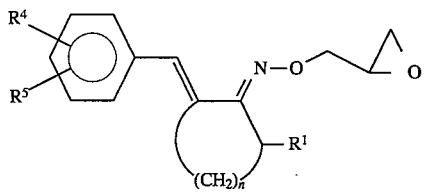

thus obtained, wherein $R^1$, $R^4$, $R^5$ and n are as stated above, with an amine of general formula (IV),

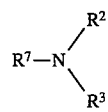

wherein $R^7$ stands for hydrogen, $R^2$ and $R^3$ are as stated above;

d) for the preparation of compounds of general formula (I), wherein R represents hydrogen or $C_{1-4}$ alkyl, reacting a cycloalkane derivative of general formula (II), wherein $R^1$, $R^4$, $R^5$ and n are as stated above and X stands for a group of formula =N—OH, with a substituted alkane of general formula (III), wherein D and $R^6$ each stands for halogen while A and R are as stated above, in the presence of a basic condensing agent, and reacting the thus-obtained halo compound with an amine of general formula (IV) wherein $R^2$, $R^3$ and $R^7$ are as stated above and, if possible and desired, converting a compound of general formula (I) thus obtained into a pharmaceutically acceptable acid-addition salt or quaternary ammonium derivative thereof, or liberating the base of general formula (I) from a salt thereof and/or separating the stereo and/or optically active isomers.

According to variant a) of the process of the invention a cycloalkane derivative of general formula (II) containing oxygen or sulfur in the place of X is reacted with a substituted alkane of general formula (III) containing a group of formula $H_2N$—O— in the place of D or with an acid-addition salt thereof. In the latter case the reaction is carried out in the presence of a basic condensing agent. The reaction is preferably carried out in an inert solvent or in a mixture of such solvents. For this purpose e.g. aliphatic alcohols (e.g. methanol or ethanol), pyridine or triethylamine can be used. As basic condensing agent preferably an organic base (e.g. pyridine, piperidine or morpholine) is applied. If the solvent is an organic base, it may serve as condensing agent, too.

According to variant b) of the process of the invention compounds of general formula (I) containing hydrogen or $C_{1-4}$ alkyl in the place of R can be prepared by reacting a compound of general formula (II), wherein X stands for a group of formula =N—OH with a compound of general formula (III), wherein R is hydrogen or $C_{1-4}$ alkyl and D stands for halogen. The reaction is performed in the presence of a basic condensing agent. For this purpose alkali amides (preferably sodium amide), alkali hydrides (preferably sodium hydride), alkali metals, alkali hydroxides (preferably sodium hydroxide) or the mixtures thereof (such as 9:1–1:9 mixtures of sodium hydroxide and potassium hydroxide) can be applied.

The reaction is carried out in an inert solvent. For this purpose aliphatic or cyclic ethers (e.g. diisopropylether, dibutylether, dioxane, tetrahydrofuran), aromatic hydrocarbons (e.g. benzene, toluene, xylene), dimethylformamide, dimethyl acetamide, dimethyl sulfoxide or possible mixtures thereof can be used.

According to variant c) of the process of the invention compounds of general formula (I) containing a hydroxy group in the place of R are prepared. For this purpose a compound of general formula (II), wherein X stands for a group of formula =N—OH is reacted with a compound of general formula (III), wherein D represents halogen, and A, $R^6$ and R together form a group of formula —$CH_2$—O—. The reaction is carried out in the presence of a basic condensing agent. The thus-obtained epoxy compound of general formula (V) is then reacted with an amine of general formula (IV).

The reaction of the compounds of general formulae (II) and (III) is performed in an inert or relatively inert solvent. As inert solvent alcohols (preferably ethanol), benzene, toluene, xylene or aliphatic cyclic ethers are used. As basic condensing agent an alkali amide (preferably sodium amide) or an alkali hydride (preferably sodium hydride) is used. Alkali metals can also be used as condensing agents. If an alkali hydroxide is applied as condensing agent, water may also serve as solvent (in such a case water is a relatively inert solvent, as on increasing the reaction time and temperature it goes into reaction with the epoxy compound).

The reaction of the compounds of general formulae (IV) and (V) can be preferably carried out also in an inert solvent, e.g. in an alcohol (preferably ethanol), acetonitrile, dioxane, tetrahydrofuran etc., but when using amines having high boiling point it can also be carried out without using any solvent. In such cases an excess of the applied amine serves as solvent.

The reaction temperature may be varied within a wide interval. It can be room temperature but an optimal rate of reaction can be achieved at the boiling point of the reaction mixture.

The new cycloalkane derivatives of general formula (I) can be transformed into pharmaceutically acceptable acid-addition salts or quaternary ammonium derivatives by methods known per se. For the preparation of the pharmaceutically acceptable acid-addition salts hydrogen halides, sulfuric acid, phosphoric acid, tartaric acid, succinic acid, acetic acid, fumaric acid, maleic acid, methanesulfonic acid, propionic acid etc. can be used. For the preparation of quaternary ammonium compounds the compounds of general formula (I) are reacted with reactants suitable for quaternarization, e.g. with alkyl halides.

The new cycloalkane derivatives of general formula (I) may comprise one or two asymmetric carbon atoms depending on the character of the substituents, thus they can be prepared in optically active forms, too. The invention covers all of the racemic or optically active forms of the compounds of general formula (I). If the former compounds or intermediates are prepared in the form of a diastereomeric mixture, they can be separated into racemic or optically active isomers in a manner known per se, e.g. by fractional distillation, crystallization, chromatography or by forming diastereomeric salts with the aid of optically active acids such as tartaric acid, dibenzoyl-tartaric acid or camphorsulfonic acid.

The compounds of general formula (II) containing oxygen or sulfur in the place of X are known and can be prepared e.g. according to the method described in J. Chem. Soc. 1955, 1126 or in J. Am. Chem. Soc. 77, 624 (1955). The compounds of general formula (III), wherein R is hydroxy, are prepared as described in J. Pharm. Sci. 58, 138 (1969). The compounds of general formula (III), wherein D stands for a group of formula $H_2N$—O— can be prepared as described in J. Pharm. Sci. 58, 138 (1969).

The compounds of general formula (II) containing a group of formula =N—OH in the place of X used as starting compounds for process variants b) and c) can be prepared e.g. according to the method described in Org. Synth. Coll. Col. II, 70. The compounds of general formula (III), wherein D stands for halogen can be prepared as described in Helv. Chim. Acta 41, 1072–1108 (1958) or in Bellstein 17, 1/V 20.

The compounds of general formula (I) possess a considerable gastric-acid-secretion inhibiting activity. They are also potent inhibitors of the gastric $H^+K^+$-ATP-ase, at the same time their toxicity is slight, so they can be used as active ingredients for the preparation of pharmaceutical compositions.

The biological activity of the new compounds according to the invention is shown by the following tests:

I. Toxicity

The test was carried out according to the method of Lichtfield and Wilcoxon [Lichtfield, J. T. and Wilcoxon, F. W.: J. Pharmacol. Exp. Ther., 96, 99 (1949)] by using white mice belonging to the CFLP strain and weighing 10 to 22 g, 10 animals per dose. The test compounds were administered orally in a volume of 20 cm$_3$/kg. After treatment the animals were observed for a period of 14 days. The results are summarized in Table I.

TABLE I

| Toxicity on mice | | |
|---|---|---|
| Compound (No. of Example) | LD$_{50}$ i.p. | mg/kg p.o. |
| 31 | >300 | >1000 |
| 44 | 100–300 | >1000 |
| 9 | about 300 | 600 |
| 34 | 88 | about 1000 |
| 35 | 100–300 | >1000 |
| 40 | 100–300 | >1000 |
| 41 | 100–300 | >1000 |

II. Gastric ulcer inhibiting effect

Test methods:

1. H$^+$/K$^+$-ATP-ase inhibition on pig'stomach. The test was carried out according to the method of Rabon and Sachs [E. C. Rabon, W. B. I. and G. Sachs: Preparation of gastric H$^+$/K$^+$-ATP-ase. Methods in Enzymology, 157, 649–651 (1988)]. The activity of the prepared enzyme was measured both in the presence and in the absence of K$^+$ ions. The difference in the liberation of phosphorus representing the activity of the enzyme was measured.

2. The gastric-acid-secretion test was carried out on rats according to the method of Shay et al. [Shay, H., Komarov, S. A., Fels, S. S., Meranze, D., Gruenstein, M., Siplet, H.: Gastroenterology 5, 43–61 (1945)]. The liberated gastric acid content was determined by titration 4 hours after the ligature of the duodenum.

3. The cytoprotective effect was determined on rats according to the method of Robert [Robert, A.: Cytoprotection by prostaglandins. Gastroenterology 77, 761–767 (1979)]. Rats weighing 200 to 250 g were used as test animals. 1 cm$^3$ of abs. ethanol was introduced to the stomach to produce an erosion of the stomach wall. The length and frequency of the lesions (erosion index and frequency) were measured and the percentage inhibition of lesion formation compared with vehicle-treated animals was calculated.

4. Measurement of $^{14}$C-aminopyrine accumulation by parietal cells. Gastric mucosal cells were prepared from rat stomach. Wistar rats (130–160 g) were killed by decapitation, the stomachs were rapidly excised and their contents were washed out with saline. The stomachs were then everted and filled with 2.5 mg/ml of pronase-containing buffer. These sacs were incubated for 60 minutes at 37° C. in carbogen-gassed medium. This incubation was followed by gentle stirring at room temperature for 45 minutes by a magnetic stirrer in order to disperse the cells from the mucosa of the everted stomachs digested only from the serosal side. The viability of the cells was determined by trypan-blue exclusion test. The percentage of the parietal cells was determined on the basis of their morphological characteristics.

Acid production of the cells prepared in this way could be induced by cyclic AMP, histamine (in the presence of 3-isobutyl-1-methylxanthine) or carbachol. The acid production was assessed by measuring the accumulation of $^{14}$C-aminopyrine. The undissociated weak base can penetrate into the acid-containing compartments of the cells. In the acidic compartment the aminopyrine dissociates and for the dissociated form the membrane is impermeable. Thus, the distribution of $^{14}$C-aminopyrine between the extracellular and intracellular spaces is an indirect quantitative index for the cellular acid production [W. Schepp, J. Schmidtler, C. Tatge, V. Schusdziarra and M. Classen: Am. J. Physiol. 259 (Gastrointest. Liver Physiol. 22) G646–G654 (1990)].

Results

1. The compounds according to the invention are potent inhibitors of the H$^+$K$^+$-APT-ase (proton pump), the IC$_{50}$ values are between 5 and 30 µM. The compounds inhibit the induced acid production on isolated parietal cells (inhibition of $^{14}$C-aminopyrine accumulation) in low concentration.

TABLE II

| Inhibition of H$^+$K$^+$-ATP-ase on partially purified pig's microsome specimen | |
|---|---|
| Compound (No. of Example) | IC$_{50}$ (µM) |
| 31 | >30 |
| 44 | 10 |
| 9 | >30 |
| 34 | 5 |
| 35 | 13 |
| 40 | 7 |
| 41 | 17 |

2. Considering the acid-secretion inhibiting effect the ED$_{50}$ values of our most effective compounds are 1.1 and 5.4 mg/kg (when administered intraduodenally). This proves that the compounds are favourable acid-secretion inhibitors in vivo.

3. The cytoprotective effect of the compounds is significant, and according to the literature (D. E. Wilson: Therapeutic aspects of prostaglandins in the treatment of peptic ulcer disease. Dig. Dis. Sci. 1986. 31, 42–46S) this is a favourable characteristic considering the potential therapeutic utility.

TABLE III

| Gastric-acid-secretion inhibiting and cytoprotective effects | | | |
|---|---|---|---|
| Compound (No. of Example) | Acid-secretion inhibition, ED$_{50}$ mg/kg, p.o. | Ethanol erosion ED$_{50}$, p.o. | Ratio of acid-secretion inhibition and erosion inhibition |
| 31 | 200 | 3.9 | 50 |
| 44 | 50–200 | 1.6 | 31 to 125 |
| 9 | 30–120 | 1.2 | 25–100 |
| 34 | 102.7 | 1.4 | 73.4 |
| 35 | <200 | 2.9 | ≦70 |
| 40 | 52.9 | 2.6 | 20 |
| Omeprazole | 3.9 | 4.5 | 0.9 |
| Cimetidine | 59.1 | 100–200 | 0.3–0.6 |
| Pirenzepine | 7.9 | 18.6 | 0.4 |
| Sucralfate | — | 69.0 | — |

From the above test results it can be established that the compounds according to the invention are only slightly toxic, at the same time they inhibit the gastric-acid secretion at doses 5 to 30 times lower than the toxic doses (LD$_{50}$). From the low ED$_{50}$ values obtained in the ethanol erosion test it can be seen that the cytoprotective effect of the test compounds is highly superior to their gastric-acid-secretion activity. Our compounds are somewhat less potent inhibitors of the gastric-acid secretion than omeprazole or pirenzepine, but considering the inhibition of the erosion of the stomach wall produced by ethanol they are superior to both reference substances. From this fact it appears that the mechanism of the effect of the new compounds is different from that of the known substances exerting an antiulceric activity. The difference demonstrated by the gastric-acid-secretion inhibition/erosion inhibition ratios is very favourable, especially in the treatment of human diseases wherein the injury of the stomach wall occurs simultaneously with a decreased acid production (e.g. gastric disorders caused by alcoholism).

Summarizing what has been said it can be established that the compounds according to the invention inhibit the enzyme responsible for the acid production in low concentrations. They are also effective in vivo and exhibit a gastric-acid-secretion inhibiting activity at considerably lower doses than the acute toxic doses. Their cyto-protective activity is excellent. Accordingly, proton-pump-inhibiting and cytoprotective substances have been found, which a) are chemically different from the hitherto known molecules possessing similar activities, so such effects could not be aforeseen on the basis of the chemical structure, b) possess an enzyme-inhibiting activity being of µM order of magnitude under the experimental conditions used, c) have an outstanding cytoprotective effect independent of the proton-pump-inhibiting activity.

According to a further aspect of the present invention there are provided pharmaceutical compositions comprising as active ingredient at least one compound of general formula (I) or a pharmaceutically acceptable acid-addition salt and/or quaternary ammonium derivative thereof in admixture with suitable inert solid or liquid pharmaceutical carriers.

The pharmaceutical compositions of the present invention can be prepared by methods known per se by admixing the active ingredient with suitable inert solid or liquid carriers or diluents and bringing the mixture to galenic form.

The compounds of general formula (I) can preferably be used in therapy orally in the form of tablets or dragées. The daily dose can vary within wide ranges depending on several factors, e.g. on the activity of the active ingredient, the patient's condition and age, the severity of the disease etc. The oral dose is generally 1 to 300 mg/day. It has to be stressed that the above doses are only of informative character and the administered dose must always be determined by the physician therapeutist.

The compounds of general formula (I) can be used in therapy in the form of solution or suspension as well. They can serve as active ingredients for the preparation of pharmaceutical compositions useful in the treatment of disorders caused by hyperacidity (gastric or duodenal ulcer), in the treatment of gastric mucosa caused by anti-phlogistics (glucocorticoids, salicylic acid derivatives) or for the mitigation of gastric disorders caused by alcoholism.

According to a further aspect of the present invention there is provided the use of the compounds of the general formula (I) or pharmaceutically acceptable salts and/or quaternary ammonium derivatives thereof for the preparation of pharmaceutical compositions having particularly ulcus-inhibiting effect.

According to a still further aspect of the present invention there is provided a method of ulcus-inhibiting and anxiolytic treatment, which comprises administering to the patient an effective amount of a compound of general formula (I) or a pharmaceutically acceptable salt thereof.

The invention is further illustrated by the following Examples of non-limiting character.

EXAMPLE 1

(R,S)-6-(E)-Phenylmethylene-2-methyl-1-(E)-[3-dimethylamino)-propoxyimino]-cyclohexane 6-(E)-Phenylmethylene-2-methylcyclohexan-1-one-(E)-oxime (21.53 g; 0.1 mole) is transformed into a salt with the aid of sodium hydride (4.8 g; 0.1 mole, 50% oily dispersion) in the mixture of 30 cm$^3$ of dimethylformamide and 20 cm$^3$ of benzene, and the salt thus obtained is reacted with 3-chloro-N,N-dimethylpropylamine (13.38 g; 0.11 mole) at the boiling point of the mixture. The boiling is continued until the starting oxime cannot be detected in the reaction mixture by thin layer chromatography (benzene:methanol 4:1, Kieselgel 60 $F_{254}$).

Yield: 27.0 g (89.7%).

(E)-2-Butenedioate (1/1) M.p.: 116° to 118.5° C.

Analysis for the formula $C_{23}H_{32}N_2O_5$ (416.51): Calculated: C %=66.32 H %=7.75 N %=6.73 Found: C %=66.55 H %=7.74 N %=6.60.

UV: $\lambda_{max}$=273 nm ($\epsilon$=17469).

EXAMPLE 2

(R,S)-6-(E)-Phenylmethylene-2-methyl-1-(E)-[3-(dimethylamino)-2-methylpropoxyimino]-cyclohexane One proceeds as specified in Example 1 except that instead of 3-chloro-N,N-dimethylpropylamine 3-chloro-2,N,N-trimethylpropylamine (14.92 g; 0.11 mole) is used.

Yield: 27.82 g (88.60%).

(E)-2-Butenedioate (1/1) M.p.: 162° to 167° C.

Analysis for the formula $C_{24}H_{34}N_2O_5$ (430.53): Calculated: C %=66.95 H %=7.96 N %=6.51 Found: C %=66.35 H %=7.96 N %=6.53.

UV: $\lambda_{max}$=273 nm ($\epsilon$=16663).

EXAMPLE 3

(R,S)-6-(E)-Phenylmethylene-2-methyl-1-(E)-(3-morpholino-propoxyimino)-cyclohexane One proceeds as specified in Example 1 except that instead of 3-chloro-N,N-dimethylpropylamine N-(3-chloropropyl)-morpholine (18.00 g; 0.11 mole) is used.

Yield: 31.23 g (91.19%).

(E)-2-Butenedioate (1/1) M.p.: 146° to 150° C.

Analysis for the formula $C_{25}H_{34}N_2O_6$ (458.54): Calculated: C %=65.47 H %=7.47 N %=6.11 Found: C %=65.20 H %=7.50 N %=6.34

UV: $\lambda_{max}$=270 nm ($\epsilon$=16019).

EXAMPLE 4

(R,S)-6-(E)-Phenylmethylene-2-methyl-1-(E)-(2-pyrrolidinyl-ethoxyimino)-cyclohexane One proceeds as specified in Example 1 except that instead of 3-chloro-N,N-dimethylpropylamine N-(2-chloroethyl)-pyrrolidine (14.7 g; 0.11 mole) is used.

Yield: 19.86 g (63.56%).

(E)-2-Butenedioate (1/1) M.p.: 140° to 146° C.

Analysis for the formula $C_{24}H_{32}N_2O_5$ (428.52): Calculated: C %=67.26 H %=7.53 N %=6.54 Found: C %=66.87 H %=7.50 N %=6.30.

UV: $\lambda_{max}$=270 nm ($\epsilon$=32776).

EXAMPLE 5

(R,S)-6-(E)-Phenylmethylene-2-methyl-1-(E)-(2-piperidinyl-ethoxyimino)-cyclohexane One proceeds as specified in Example 1 except that instead of 3-chloro-N,N-dimethylpropylamine N-(2-chloroethyl)-piperidine (16.24 g; 0.11 mole) is used.

Yield: 32.32 g (99.01%).

(E)-2-Butenedioate (1/1) M.p.: 170.5° to 175.5° C.

Analysis for the formula $C_{25}H_{34}N_2O_5$ (442.54): Calculated: C %=67.85 H %=7.74 N %=6.33 Found: C %=66.64 H %=7.65 N %=6.22

UV: $\lambda_{max}$=270 nm ($\epsilon$=17753).

EXAMPLE 6

(R,S)-6-(E)-Phenylmethylene-2-methyl-1-(E)-[2-hexahydro-1H-azepinyl)-ethoxyimino]-cyclohexane One proceeds as specified in Example 1 except that instead of 3-chloro-N,N-dimethylpropylamine N-(2-chloroethyl)-hexahydro-1H-azepine (17.78 g; 0.11 mole) is used.

Yield: 31.7 g (93.11%).

(E)-2-Butenedioate (2/1) M.p.: 144° to 150° C.

Analysis for the formula $C_{24}H_{34}N_2O_3$ (426.55): Calculated: C %=67.57 H %=8.03 N %=6.67 Found: C %=67.22 H %=8.09 N %=6.63.

UV: $\lambda_{max}$=266 nm ($\epsilon$=14757).

EXAMPLE 7

(R,S)-6-(E)-Phenylmethylene-2-methyl-1-(E)-[3-(dimethylamino)-2-hydroxypropoxyimino]-cyclohexane a) 6-(E)-Phenylmethylene-2-methylcyclohexan-1-one-(E)-oxime (21.53 g; 0.1 mole) is transformed into a salt with sodium hydride (4.8 g; 0.1 mole, 50% oily dispersion) in the mixture of dimethylformamide and benzene, and the salt thus obtained is reacted with 1-chloro-2,3-epoxypropane (10.18 g; 0.11 mole) at a temperature between 40° C. and 50° C. The stirring is continued until the starting oxime cannot be detected in the reaction mixture by thin layer chromatography (Kieselgel 60 $F_{254}$, n-hexane:dioxane 4:1). The reaction mixture is washed three times with 50 cm$^3$ of water each and the solvent is distilled off.

Yield: 27.03 g (99.61%).

b) To a solution of the product obtained according to the method described in paragraph a) (27.03 g; 0.099 mole) and dimethylamine hydrochloride (9.87 g; 0.12 mole) in ethanol triethylamine (12.14 g; 0.12 mole) is dropped and the mixture is slowly heated to the boiling point. The boiling is continued until the starting oxime cannot be detected in the reaction mixture by thin layer chromatography (benzene:methanol 4:1, Kiselgel 60 $F_{254}$).

Yield: 18.36 g (58.02%).

(E)-2-Butenedioate (2/1) M.p.: 126° to 149° C.

Analysis for the formula $C_{42}H_{60}N_4O_8$ (748,94): Calculated: C %=67.35 H %=8.08 N %=7.48 Found: C %=67.31 H %=8.10 N %=7.40.

UV: $\lambda_{max}$=279 nm ($\epsilon$=31713).

EXAMPLE 8

(R,S)-6-(E)-(4-Fluorophenylmethylene)-2-methyl-1-(E)-(2-morpholinoethoxyimino)-cyclohexane One proceeds as specified in Example 1 except that instead of 6-(E)-phenylmethylene-2-methylcyclohexan-1-one-(E)-oxime 6-(E)-(4-fluorophenylmethylene)-2-methylcyclohexan-1-one-(E)-oxime (23.32 g; 0.1 mole) and instead of 3-chloro-N,N-dimethylpropylamine 4-(2-chloroethyl)-morpholine (16.46 g; 0.11 mole) is used.

Yield: 18.90 g (54.54 %).

(E)-2-Butenedioate (1/1) M.p.: 139° to 145° C.

Analysis for the formula $C_{24}H_{31}FN_2O_6$ (462.51): Calculated: C %=62.32 H %=6.76 N %=6.06 F %=4.11 Found: C %=61.72 H %=6.71 N %=6.07 F %=4.00.

UV: $\lambda_{max}$=270 nm ($\epsilon$=16751).

EXAMPLE 9

(R,S)-6-(E)-(4-Fluorophenylmethylene)-2-methyl-1-(E)-[3-(dimethylamino)-2-methylpropoxyimino]-cyclohexane One proceeds as specified in Example 8 except that instead of 4-(2-chloroethyl)-morpholine 3-chloro-2,N,N-trimethylpropylamine (14.92 g; 0.11 mole) is used.

Yield: 32.59 g (98.03%).

(E)-2-Butenedioate (1/1) M.p.: 188° C.

Analysis for the formula $C_{24}H_{33}FN_2O_5$ (448.52): Calculated: C %=64.26 H %=7.41 N %=6.25 F %=4.24 Found: C %=64.55 H %=7.43 N %=6.47 F %=4.20.

UV: $\lambda_{max}$=290 nm ($\epsilon$=1611).

EXAMPLE 10

(R,S)-6-(E)-(4-Chlorophenylmethylene)-2-methyl-1-(E){2-[bis-(1-methylethyl)-amino]-ethoxyimino}-cyclohexane 6-(E)-(4-Chlorophenylmethylene)-2-methylcyclohexan-1-one-(E)-oxime (24.95 g; 0.1 mole) is transformed into a salt with freshly prepared sodium methylate (5.4 g; 0.1 mole), and this salt is reacted with N-(2-chloroethyl)-N-)1-methylethyl)-2-propylamine(18.01 g; 0.11 mole) in dimethylformamide. Further on the process of Example 1 is followed.

Yield: 33.30 g (88.45%).

(E)-2-Butenedioate (1/1) M.p.: 133° to 138° C.

Analysis for the formula $C_{26}H_{37}ClN_2O_5$ (493.04): Calculated: C %=63.33 H %=7.56 N %=5.68 Cl %=7.19 Found: C %=63.20 H %=7.71 N %=5.95 Cl %=7.21.

UV: $\lambda_{max}$=276 nm ($\epsilon$=19782).

EXAMPLE 11

(R,S)-6-(E)-(4-Chlorophenylmethylene)-2-methyl-1-(E)-[3-(4-methyl-1-piperazinyl)-propoxyimino]-cyclohexane 6-(E)-(4-Chlorophenylmethylene)-2-methyl-1-(E)-cyclohexan-1-one-(E)-oxime (24.95 g; 0,1 mole) is transformed into a salt with sodium hydride (4.8 g; 0.1 mole, 50% oily dispersion) in the mixture of dimethylformamide and benzene, and the salt thus obtained is reacted with 1-bromo-3-chloropropane (15.74 g; 0,1 mole) at a temperature of 60° C. until the starting oxime cannot be detected any more in the reaction mixture. Then it is cooled, washed three times with 50 cm$^3$ of water each and evaporated in vacuo. The thus-obtained 6-(E)-(4-chlorophenylmethylene)-2-methyl-1-(E)-(3-chloropropoxyimino)-cyclohexane (29.12 g; 89.52%) is reacted with N-methylpiperazine (10.01 g; 0.1 mole) in ethanol at the boiling point of the reaction mixture.

Yield: 21.65 g (55.52%) M.p.: 88° to 91° C.

(E)-2-Butenedioate (1/2) M.p.: 221° C. (decomp.).

Analysis for the formula $C_{30}H_{40}ClN_3O_9$ (622.1): Calculated: C %=57.92 H %=6.48 N %=6.75 Cl %=5.70 Found: C %=58.16 H %=6.30 N %=6.84 Cl %=5.63.

UV: $\lambda_{max}$=270 nm ($\epsilon$=19408).

EXAMPLE 12

(R,S)-6-(E)-(4-Chlorophenylmethylene)-2-methyl-1-(E)-[3-(dimethylamino)-2-methylpropoxyimino]-cyclohexane One proceeds as specified in Example 10 except that instead of N-(2-chloroethyl)-N-(1-methylethyl)-2-propylamine 3-chloro-2,N,N-trimethylpropylamine (14.92 g; 0.11 mole) is used.

Yield: 28.15 g (80.68%).

(E)-2-Butenedioate (1/1) M.p.: 184° to 188.5° C.

Analysis for the formula $C_{24}H_{33}ClN_2O_5$ (464.977): Calculated: C %=61.99 H %=7.15 N %=6.03 Cl %=7.63 Found: C %=60.52 H %=7.01 N %=5.93 Cl %=7.54.

UV: $\lambda_{max}$=267 nm ($\epsilon$=19242).

EXAMPLE 14

(R,S)-6-(E)-(4-Bromophenylmethylene)-2-methyl-1-(E)-(3-morpholinopropoxyimino)-cyclohexane One proceeds as specified in Example 1 except that instead of 6-(E)-phenylmethylene-2-methylcyclohexan-1-one-(E)-oxime 6-(E)-(4-bromophenylmethylene)-2-methyl-cyclohexan-1-one-(E)-oxime (29.42 g; 0.1 mole) and instead of 3-chloro-N,N-dimethylpropylamine 4-(3-chloropropyl)-morpholine (18.00 g; 0.11 mole) is used.

Yield: 41.12 g (97.58%).

(E)-2-Butenedioate (1/1) M.p.: 154°–157.5° C.

Analysis for the formula $C_{25}H_{35}BrN_2O_6$ (537.45): Calculated: C %=55.87 H %=6.19 N %=5.21 Br %=14.87 Found: C %=55.72 H %=6.13 N %=5.34 Br %=14.83.

UV: $\lambda_{max}$=274 nm ($\epsilon$=19069)

EXAMPLE 15

(R,S)-6-(E)-(2-Methoxyphenylmethylene)-2-methyl-1-(E)-[2-(dimethylamino)-ethoxyimino]-cyclohexane 6-(E)-2-(2-Methoxyphenylmethylene)-2-methylcyclohexan-1-one-(E)-oxime (24.53 g; 0.1 mole) is converted into a salt in a saturated (40%) aqueous solution of an alkali hydroxide (sodium and/or potassium hydroxide) in the presence of 20 cm³ of dimethyl sulfoxide, and the salt thus obtained is reacted with 2-chloro-N,N-dimethylethylamine (11.83 g; 0.11 mole) at the boiling point of the reaction mixture. Further on the process of Example 1 is followed.

Yield: 26.86 g (84.88%).

(E)-2-Butenedioate (1/1) M.p.: 152°–157° C.

Analysis for the formula $C_{23}H_{32}N_2O_6$ (432.51): Calculated: C %=63.87 H %=7.46 N %=6.48 Found: C %=63.87 H %=7.55 N %=6.57.

UV: $\lambda_{max}$=261 nm ($\epsilon$=12560).

EXAMPLE 16

(R,S)-6-(E)-(2-Methoxyphenylmethylene)-2-methyl-1-(E)-[3-(dimethylamino)-2-methylpropoxyimino)-cyclohexane One proceeds as specified in Example 15 except that instead of 2-chloro-N,N-dimethylethylamine 3-chloro-2,N,N-trimethylpropylamine (14.92 g; 0.11 mole) is used.

Yield: 24.51 g (71.15%).

(E)-2-Butenedioate (1/1) M.p.: 143.5°–147.5° C.

Analysis for the formula $C_{25}H_{36}N_2O_6$ (460.56): Calculated: C %=65.19 H %=7.88 N %=6.08 Found: C %=65.10 H %=7.62 N %=6.18.

UV: $\lambda_{max}$=265 nm ($\epsilon$=12871) 286 nm ($\epsilon$=9930).

EXAMPLE 17

(R,S)-6-(E)-(2,4-Dichlorophenylmethylene)-2-methyl-1-(E)-{3-[4-(phenylmethyl)-1-piperazinyl]-2-methylpropoxyimino}-cyclohexane One proceeds as specified in Example 1 except that instead of 6-(E)-phenylmethylene-2-methylcyclohexan-1-one-(E)-oxime 6-(E)-(2,4-dichlorophenylmethylene)-2-methyl-1-one-(E)-oxime (28.42 g; 0.1 mole) and instead of 3-chloro-N,N-dimethylpropylamine 1-(phenylmethyl)-4-(3-chloro-2-methyl-propyl)-piperazine (29.35 g; 0.11 mole) is used.

Yield: 20.56 g (39.96%).

(E)-2-Butenedioate (1/2) M.p.: 205° to 210° C.

Analysis for the formula $C_{37}H_{45}Cl_2N_3O_9$ (746.66): Calculated: C %=59.51 H %=6.07 N %=5.63 Cl %=9.50 Found: C %=59.83 H %=6.21 N %=5.77 Cl %=9.35.

UV: $\lambda_{max}$=248 nm ($\epsilon$=12161).

EXAMPLE 18

(R,S)-6-(E)-(2-Methoxy-4-ethoxyphenylmethylene)-2-methyl-1-(E)-{3-[4-(phenylmethyl)-1-piperazinyl]-propoxyimino}-cyclohexane One proceeds as specified in Example 1 except that instead of 6-(E)-phenylmethylene-2-methyl-1-one-(E)-oxime 6-(E)-(2-methoxy-4-ethoxyphenylmethylene)-2-methyl-1-one-(E)-oxime (28.94 g; 0.1 mole) and instead of 3-chloro-N,N-dimethylpropylamine 1-(phenylmethyl)-4-(3-chloropropyl)-piperazine (27.81 g; 0.11 mole) is used.

Yield: 34.25 g (67.73%).

Hydrochloride (1/2) M.p.: 193°–199° C.

Analysis for the formula $C_{31}H_{45}Cl_2N_3O_3$ (578.60): Calculated: C %=64.35 H %=7.84 N %=7.26 Cl %=12.25 Found: C %=64.34 H %=7.63 N %=7.19 Cl %=12.12.

UV: $\lambda_{max}$=292 nm ($\epsilon$=16837).

EXAMPLE 19

(R,S)-6-(E)-Phenylmethylene-2-ethyl-1-(E)-[3-(dimethylamino)-2-methylpropoxyimino]-cyclohexane One proceeds according to Example 2 except that instead of benzene toluene is used and instead of 6-(E)-phenylmethylene-2-methylcyclohexan-1-(E)-oxime 6-(E)-phenylmethylene-2-ethyl-cyclohexan-1-one-(E)-oxime (22.93 g; 0.1 mole) is applied as starting substance.

Yield: 22.43 g (68.28%).

(E)-2-Butenedioate (1/1) M.p.: 98°–101° C.

Analysis for the formula $C_{25}H_{36}N_2O_5$ (444.56): Calculated: C %=67.54 H %=8.16 N %=6.30 Found: C %=67.58 H %=8.04 N %=6.30.

UV: $\lambda_{max}$=268 nm ($\epsilon$=15620).

EXAMPLE 20

(R,S)-6-(E)-phenylmethylene-2-ethyl-(E)-[3-(4-methyl-1-piperazinyl)-2-methylpropoxyimino]-cyclohexane One proceeds as specified in Example 19 except that instead of 3-chloro-2-methylpropyl-N,N-dimethylamine 1-(3-chloro-2-methylpropyl)-4-methylpiperazine (20.98 g; 0.11 mole) is used as starting substance.

Yield: 29.52 g (76.95%).

(E)-2-Butenedioate (1/2) M.p.: 195°–200° C.

Analysis for the formula $C_{32}H_{45}N_3O_9$ (615.7): Calculated: C %=62.42 H %=7.37 N %=6.82 Found: C %=61.91 H %=6.93 N %=6.77.

UV: $\lambda_{max}$=267 nm ($\epsilon$=15277).

EXAMPLE 21

(R,S)-6-(E)-(4-Methoxyphenylmethylene)-2-propyl-1-(E)-{2-[4-(phenylmethyl- 1-piperazinyl]-ethoxyimino}-cyclohexane One proceeds as specified in Example 1, except that instead of benzene toluene is used, instead of 6-(E)-phenylmethylene-2-methylcyclohexan-1-one-(E)-oxime 6-(E)-)4-methoxyphenylmethylene)-2-propyl-1-one-(E)-oxime (27.34 g; 0.1 mole) and instead of 3-chloro-N,N-dimethylpropylamine 1(phenylmethyl)-4-(2-chloroethyl-piperazine (26.26 g; 0.11 mole) is applied.

Yield: 34.65 g (72.85%).

(E)-2-Butenedioate (1/2) M.p.: 188°–192° C.

Analysis for the formula $C_{38}H_{49}N_3O_{10}$ (707.79): Calculated: C %=64.48 H %=6.98 N %=5.94 Found: C %=64.44 H %=7.00 N %=6.04.

UV: $\lambda_{max}$=281 nm ($\epsilon$=19640).

EXAMPLE 22

(R,S)-6-(E)-(4-methoxyphenylmethylene)-2-propyl-1-(E)-[2-(hexamethyleneimino)-ethoxyimino]-cyclohexane One proceeds as specified in Example 21 except that instead of 1-(phenylmethyl)-4-(2-chloroethyl)-piperazine N-(2-chloroethyl)-hexahydro-1H-azepine (17.78 g; 0.11 mole) is used.

Yield: 33.73 g (84.63%).

(E)-2-Butenedioate (1/1) M.p.: 151°–154° C.

Analysis for the formula $C_{29}H_{42}N_2O_6$ (514.65): Calculated: C %=67.68 H %=8.23 N %=5.44 Found: C %=67.22 H %=8.40 N %=5.44.

UV: $\lambda_{max}$=281 nm ($\epsilon$=20840).

EXAMPLE 23

(R,S)-6-(E)-Phenylmethylene-2-butyl-1-(E)-[3-(dimethylamino)-propoxyimino]-cyclohexane A solution of 6-(E)-phenylmethylene-2-butylcyclohexan-1-one (24.24 g; 0.1 mole) and O-[3-(dimethylamino)-propyl]-hydroxylamine (11.81 g; 0.1 mole) in ethanol is reacted at the boiling point of the mixture until the starting substance cannot be detected in it by thin layer chromatography (Kieselgel 60 $F_{245}$, benzene:methanol 4:1). Then fumaric acid ( 11.60 g; 0.1 mole) is added to the mixture and the separated crystals are filtered.

Yield: 26.55 g (77.5%).

(E)-2-Butenedioate (1/1) M.p.: 112.7° to 115° C.

Analysis for the formula $C_{26}H_{38}N_2O_5$ (458.58): Calculated: C %=68.09 H %=8.35 N %=6.11 Found: C %=68.10 H %=8.13 N %=5.88.

UV: $\lambda_{max}$=270 nm.

EXAMPLE 24

(R,S)-6-(E)-phenylmethylene-2-butyl-1-(E)-[3-(4-methyl-1-piperazinyl)-propoxyimino]-cyclohexane One proceeds as specified in Example 1 except that instead of 6-(E)-phenylmethylene-2-methylcyclohexan-1-one-(E)-oxime 6-(E)-phenylmethylene-2-butylcyclohexan-1-on-(E)-oxime (25.32 g; 0.1 mole) and instead of 3-chloro-N,N-dimethyl-propylamine 1-(3-chloropropyl)-4-methylpiperazine (19.44 g; 0.11 mole) is used.

Yield: 29.0 g (56.45%).

(E)-2-Butenedioate (1/2) M.p.: 182° to 197.2° C.

Analysis for the formula $C_{33}H_{43}N_3O_9$ (629.76): Calculated: C %=62.96 H %=7.47 N %=6.67 Found: C %=63.60 H %=7.61 N %=6.78.

UV: $\lambda_{max}$=268 nm ($\epsilon$=16700).

EXAMPLE 25

(R,S)-6-(E)-phenylmethylene-2-butyl-1-(E)-{2-[bis-(1-methylethyl)-amino]-ethoxyimino}-cyclohexane One proceeds as specified in Example 24 except that instead of 1-(3-chloropropyl)-4-methyl-piperazine N-(2-chloro-ethyl)-N-(1-methylethyl)-2-propylamine (18.01 g; 0.11 mole) is used.

Yield: 34.50 g (89.70%).

Hydrochloride (1/1) M.p.: 127°–132° C.

Analysis for the formula $C_{25}H_{41}ClN_2O$ (421.06): Calculated: C %=71.31 H %=9.82 N %=6.65 Cl %=8.42 Found: C %=71.22 H %=9.97 N %=6.59 Cl %=8.26.

UV: $\lambda_{max}$=273 nm ($\epsilon$=16215).

EXAMPLE 26

(R,S)-6-(E)-Phenylmethylene-2-butyl-1-(E)-[3-(4-phenylmethyl-1-piperazinyl)-propoxyimino]-cyclohexane One proceeds as specified in Example 24 except that instead of 1-(3-chloropropyl)-4-methyl-piperazine 4-phenylmethyl)-1-(3-chloropropyl)-piperazine (27.81 g; 0.11 mole) is used.

Yield: 43.21 g (91.22%).

Dihydrochloride (1/2) M.p.: 188° to 193° C.

Analysis for the formula $C_{31}H_{45}ClN_3O$ (546.64): Calculated: C %=68.11 H %=8.30 N %=7.69 Cl %=12.97 Found: C %=67.51 H %=8.59 N %=7.45 Cl %=12.36.

UV: $\lambda_{max}$=273 nm ($\epsilon$=15830).

EXAMPLE 27

(R,S)-6-(E)-Phenylmethylene-2-butyl-1-(E)-[2-(dimethylamino)-ethoxyimino]-cyclohexane One proceeds as specified in Example 24 except that instead of 1-(3-chloropropyl)-4-methyl-piperazine 2-chloro-N,N-dimethylethylamine (11.83 g; 0.11 mole) is used.

Yield: 15.71 g ( 49.64%).

Hydrochloride (1/1) M.p.: 132° to 150° C.

Analysis for the formula $C_{20}H_{33}ClN_2O$ (352.94): Calculated: C %=68.05 H %=9.42 N %=7.94 Cl %=10.05 Found: C %=68.80 H %=9.25 N %=7.84 Cl %=9.66.

UV: $\lambda_{max}$=273 nm ($\epsilon$=15180).

EXAMPLE 28

(R,S)-6-(E)-(4-Chlorophenylmethylene)-2-butyl-1-(E)-[3-(dimethylamino)-2-methylpropoxyimino]-cyclohexane One proceeds as specified in Example 1 except that instead of 6-(E)-phenylmethylene-2-methylcyclohexan-1-one-(E)-oxime 6-(E)-(4-chlorophenylmethylene)-2-butylcyclohexan-1-one-(E)-oxime (29.19 g; 0.1 mole) and instead of 3-chloro-N,N-dimethylpropylamine 3-chloro-2-N,N-trimethylpropylamine (14.92 g; 0.11 mole) is used.

Yield: 29.43 g (75.27%).

(E)-2-Butenedioate (1/1) M.p.: 134° to 143° C.

Analysis for the formula $C_{27}H_{39}ClN_2O_5$ (507.063): Calculated: C %=63.95 H %=7.75 N %=5.53 Cl %=6.99 Found: C %=64.55 H %=7.84 N %=5.38 Cl %=7.03.

UV: $\lambda_{max}$=272 nm ($\epsilon$=19288).

EXAMPLE 29

(R,S)-6-(E)-(4-Chlorophenylmethylene)-2-butyl-1-(E)-(2-piperidinyl-ethoxyimino)-cyclohexane One proceeds as specified in Example 28 except that instead of 3-chloro-2,N,N-trimethylpropylamine N-(2-chloro-ethyl)-piperidine (16.24 g; 0.11 mole) is used.

Yield: 25.36 g (62.93%).

(E)-2-Butenedioate (1/1) M.p.: 160° to 165° C.

Analysis for the formula $C_{28}H_{39}ClN_2O_5$ (519.07): Calculated: C %=64.75 H %=7.57 N %=5.40 Cl %=6.83 Found: C %=64.52 H %=7.43 N %=5.39 Cl %=6.86.

UV: $\lambda_{max}$=272 nm ($\epsilon$=19980).

EXAMPLE 30

(R,S)-6-(E)-(4-Chlorophenylmethylene)-2-butyl-1-(E)-(2-morpholinyl-ethoxyimino)-cyclohexane One proceeds as specified in Example 28 except that instead of 3-chloro-2,N,N-trimethylpropylamine 4-(2-chloro-ethyl)-morpholine (16.46 g; 0.11 mole) is used.

Yield: 38.49 g (95.04%).

(E)-2-Butenedioate (1/1) M.p.: 145° to 148° C.

Analysis for the formula $C_{27}H_{37}ClN_2O_5$ (521.05): Calculated: C %=62.23 H %=7.16 N %=5.38 Cl %=6.81 Found: C %=62.94 H %=7.30 N %=5.57 Cl %=6.79.

UV:$\lambda_{max}$=272 nm ($\epsilon$=18944).

EXAMPLE 31

(R,S)-6-(E)-(4-Fluorophenylmethylene)-2-pentyl-1-(E)-[2-(4-phenylmethyl-1-piperazinyl)-ethoxyimino]-cyclohexane One proceeds as specified in Example 1 except that instead of benzene toluene is used, instead of 6-(E)-phenylmethylene-2-methylcyclohexan-1-one-(E)-oxime 6-(E)-(4-fluorophenylmethylene)-2-pentylcyclohexan-1-one-(E)-oxime (28.94 g; 0.1 mole) and instead of 3-chloro-N,N-dimethylpropylamine 1-(phenylmethyl)-4-(2-chloroethyl)-piperazine (26.26 g; 0.11 mole) is applied.

Yield: 39.17 g (79.67%)

(E)-2-Butenedioate (1/2) M.p.: 189°–193.5° C.

Analysis for the formula $C_{39}H_{50}FN_3O_9$ (723.81): Calculated: C %=64.71 H %=6.96 N %=5.81 F %=2.63 Found: C %=65.26 H %=7.18 N %=5.88 F %=2.50.

UV: $\lambda_{max}$=268 nm ($\epsilon$=16080).

EXAMPLE 32

(R,S)-6-(E)-Phenylmethylene-2-hexyl-1-(E)-[3-(dimethylamino)-propoxyimino]-cyclohexane One proceeds as specified in Example 1 except that instead of benzene toluene is used and instead of 6-(E)-phenylmethylene- 2-methylcyclohexan-1-one-(E)-oxime 6-(E)-phenylmethylene-2-hexylcyclohexan-1-one-(E)-oxime (28.54 g; 0.1 mole) is applied.

Yield: 27.3 g (73.70%).

Hydrochloride (1/1) M.p.: 136° to 138° C.

Analysis for the formula $C_{24}H_{39}ClN_2O$ (407.03): Calculated: C %=70.82 H %=9.66 N %=6.88 Cl %=8.71 Found: C %=71.10 H %=9.88 N %=6.91 Cl %=8.68.

UV: $\lambda_{max}$=274 nm ($\epsilon$=17789).

EXAMPLE 33

(R,S)-6-(E)-(2-Methoxyphenylmethylene)-2-hexyl-1-(E)-(2-pyrrolidinylethoxyimino)-cyclohexane One proceeds as specified in Example 1 except that instead of benzene toluene is used, instead of 6-(E)-phenylmethylene-2-methylcyclohexan-1-one-(E)-oxime 6-(E)-(2-methoxyphenylmethylene)-2-hexylcyclohexan-1-one-(E)-oxime (31.54 g; 0.1 mole) and instead of 3-chloro-N,N-dimethylpropylamine 1-(2-chloroethyl)-pyrrolidine (14.70 g; 0.11 mole) is applied.

Yield: 29.49 g (71.47%).

(E)-2-Butenedioate (1/1) M.p.: 142.5°–147° C.

Analysis for the formula $C_{30}H_{44}N_2O_6$ (528.67): Calculated: C %=68.15 H %=8.39 N %=5.30 Found: C %=67.95 H %=8.51 N %=5.47.

UV: $\lambda_{max}$=263 nm ($\epsilon$=12992).

EXAMPLE 34

(R,S)-6-(E)-(2-Methoxyphenylmethylene)-2-hexyl-1-(E)-[2-(diethylamino)-ethoxyimino]-cyclohexane One proceeds as specified in Example 33 except that instead of 1-(2-chloroethyl)-pyrrolidine 2-chloro-N,N-diethylethylamine (14.92 g; 0.11 mole) is used.

Yield: 18.98 g (45.78%).

Hydrochloride (1/1) M.p.: 155.5°–158.5 ° C.

Analysis for the formula $C_{26}H_{43}ClN_2O_2$ (451.08): Calculated: C %=69.23 H %=9.61 N %=6.21 Cl %=7.86 Found: C %=69.62 H %=9.33 N %=6.42 Cl %=7.84.

UV: $\lambda_{max}$=263 nm ($\epsilon$=12204) $\lambda_{max}$=294 nm ($\epsilon$=8844).

EXAMPLE 35

(R,S)-6-(E)-(4-Fluorophenylmethylene)-2-heptyl-1-(E)-[2-(dimethylamino)-ethoxyimino]-cyclohexane One proceeds as specified in Example 1 except that instead of 6-(E)-phenylmethylene-2-methylcyclohexan-1-(E)-oxime 6-(E)-(4-fluorophenylmethylene)-2-heptylcyclohexan-1-(E)-one oxime (31.74 g; 0.1 mole) and instead of 3-chloro-N,N-dimethylpropylamine 2-chloro-N,N-dimethylethylamine (11.83 g; 0.11 mole) is used.

Yield: 31.3 g (.80.55%).

(E)-2-Butenedioate (1/1) M.p.: 92°–99° C.

Analysis for the formula $C_{28}H_{41}FN_2O_5$ (504.63): Calculated: C %=66.64 H %=8.19 N %=5.55 R %=3.77 Found: C %=66.82 H %=8.29 N %=5.61 R %=3.70.

UV: $\lambda_{max}$=265 nm ($\epsilon$=15593).

EXAMPLE 36

(R,S)-5-(E)-(2-Methoxyphenylmethylene)-2-butyl-1-(E)-[2-(diethylamino)-ethoxyimino]-cyclopentane 5-(E)-(2-Methoxyphenylmethylene)-cyclopentan-1-one-(E)-oxime 27.24 g; 0.1 mole) is transformed into a salt with sodium amide ( 3.9 g; 0.1 mole, 50% toluene suspension) in a 1:1 mixture of dimethylformamide and toluene, and the salt thus obtained is reacted with 2-chloro-N,N-diethylethylamine (14.92 g; 0.11 mole) at the boiling point of the reaction mixture. Further on the process of Example 1 is followed.

Yield: 30.96 g (83.10%).

(E)-2-Butenedioate (1/1) M.p.: 134°–138° C.

Analysis for the formula $C_{29}H_{44}N_2O_6$ (516.66): Calculated: C %=67.42 H %=8.58 N %=5.42 Found: C %=67.75 H %=8.68 N %=5.57.

UV: $\lambda_{max}$=298 nm ($\epsilon$=15105) $\lambda_{max}$=319 nm ($\epsilon$=15717).

EXAMPLE 37

(R,S)-5-(E)-(2-Methoxyphenylmethylene)-2-butyl-1-(E)-{2-[bis-( 1-methylethyl)-amino]-ethoxyimino}-cyclopentane One proceeds as specified in Example 36 except that instead of 2-chloro-N,N-diethylethylamine N-(2-chloroethyl)-N-(1-methylethyl)-2-propylamine (18.01 g; 0.11 mole) is used.

Yield: 30.96 g (83.11%).

(E)-2-Butenedioate (1/1) M.p.: 134°–138° C.

Analysis for the formula $C_{29}H_{44}N_2O_6$ (516.66). Calculated: C %=67.42 H %=8.58 N %=5.42 Found: C %=67.75 H %=8.68 N %=5.57.

UV: $\lambda_{max}$=298 nm ($\epsilon$=15105) $\lambda_{max}$=319 nm ($\epsilon$=15717).

EXAMPLE 38

(R,S)-5-(E)-(4-Chlorophenylmethylene)-2-butyl-1-(E)-[3-(dimethylamino)-propoxyimino]-cyclopentane One proceeds as specified in Example 1 except that instead of benzene toluene is used and instead of 6-(E)-phenyl-methylenecyclohexan-1-one-(E)-oxime 5-(E)-(4-chlorophenylmethylene) -cyclopentan-1-one-(E)-oxime (27.78 g; 0.1 mole) is applied.

Yield: 27.33 g (75.31%).

(E)-2-Butenedioate (1/1) M.p.: 131°–134° C.

Analysis for the formula $C_{25}H_{35}ClN_2O_5$ (479.007): Calculated: C %=62.68 H %=7.37 N %=5.85 Cl %=7.40 Found: C %=62.32 H %=7.40 N %=5.96 Cl %=7.45.

UV: $\lambda_{max}$=305 nm ($\epsilon$=32931).

EXAMPLE 40

(R,S)-7-(E)-(4-Chlorophenylmethylene)-2-propyl-1-(E)-[2-(diethylamino)-ethoxyimino]-cycloheptane 7-(E)-(4-chlorophenylmethylene)-2-propylcycloheptane-1-one-(E) (27.98 g; 0.1 mole) is transformed into a salt with sodium hydride (4.8 g; 0.1 mole, 50% oily dispersion) in a mixture of 30 cm$^3$ of dimethylformamide and 200 cm$^3$ of benzene, and the salt thus obtained is reacted with 2-chloro-N,N-diethylethylamine (14.92 g; 0.11 mole). Further on the process of Example 1 is followed.

Yield: 32.26 g (82.5%).

(E)-2-Butenedioate (1/1) M.p.: 96°–99° C.

Analysis for the formula $C_{27}H_{39}ClN_2O_5$ (507.06): Calculated: C %=63.95 H %=7.75 N %=5.53 Cl %=6.99 Found: C %=63.3 H %=7.91 N %=5.53 Cl %=6.83.

UV: $\lambda_{max}$=240 nm ($\epsilon$=18718).

EXAMPLE 41

(R,S)-6-(E)-(3,4-Dichlorophenylmethylene)-2-methyl-1-(E)-[2-(diethylamino)-ethoxyimino]-cyclohexane One proceeds as specified in Example 40 except that instead of 7-(E)-(4-dichlorophenylmethylene)-2-propylcycloheptan-1-one-(E)-oxime 6-(E)-(3,4-dichlorophenylmethylene)-2-methylcyclohexan-1-one-(E)-oxime (29.3 g; 0.1 mole) is used.

Yield: 30.4 g (79.3%).

(E)-2-Butenedioate (1/1) M.p.: 126°–129° C.

Analysis for the formula $C_{24}H_{32}Cl_2O_5$ (499.43): Calculated: C %=57.71 H %=6.46 N %=5.61 Cl %=14.2 Found: C %=57.13 H %=6.30 N %=5.73 Cl %=14.3.

UV: $\lambda_{max}$=274 nm ($\epsilon$=10348).

EXAMPLE 42

(R,S)-6-(E)-(4-Chlorophenylmethylene-2-methyl-1-(E)-{2-[bis( 1-methylethyl)-amino]-ethoxyimino}-cyclohexane One proceeds as specified in Example 25 except that instead of 6-(E)-phenylmethylene-2-methyl-cyclohexane1-one-(E)-oxime 6-(E)-(4-chlorophenylmethylene)-2-methylcyclohexane1-one-(E)-oxime (23.57 g; 0.1 mole) is used.

Yield: 29.3 g (77.7%).

(E)-2-Butenedioate (1/1) M.p.: 127°–129° C.

Analysis for the formula $C_{26}H_{37}ClN_2O_5$ (493.04): Calculated: C %=63.33 H %=7.57 N %=5.68 Cl %=7.19 Found: C %=63.27 H %=7.68 N %=5.71 Cl %=7.06.

UV: $\lambda_{max}$=272 nm ($\epsilon$=19197).

EXAMPLE 43

(R,S)-6-(E)-(4-Chlorophenylmethylene)-2-methyl-1-(E)-[3-dimethylamino)-2-methylpropoxyimino]-cyclohexane One proceeds as specified in Example 9 except that instead of 6-(E)-(4-fluorophenylmethylene)-2-methylcyclohexan-1-one (E)-oxime 6-(E)-(4-chlorophenylmethylene)-2-methylcyclohexan-1-one-(E)-oxime (23.57 g; 0.1 mole) is used.

Yield: 22.16 g (63.5%).

(E)-2-Butenedioate (1/1) M.p.: 186°–189° C.

Analysis for the formula $C_{24}H_{33}ClN_2O_5$ (464.98): Calculated: C %=61.99 H %=7.15 N %=6.03 Cl %=7.63 Found: C %=61.52 H %=7.01 N %=5.93 Cl %=7.54.

UV: $\lambda_{max}$=276 nm ($\epsilon$=19242).

EXAMPLE 44

(R,S)-2-Propyl-7-(E)-(4-chlorophenylmethylene)-1-(E)-[2-hydroxy- 3-(N-pyrrolidinylpropoxyimino)]-cycloheptane a) One proceeds as specified in Example 7 except that 29.1 g (0.1 mole) of 2-propyl-7-(E)-(4-chlorophenylmethylenecycloheptan-1-one-(E)-oxime is used as oxime.

Yield: 34.3 g (99.5%)

b) To a solution of the product obtained as specified above 14.22 g (0.2 mole) of pyrrolidine are added and the reaction mixture is boiled for 8 hours.

Yield: 32.85 g (78%). 2-(E)-Butenedioate (1/1) M.p.: 166°–168.5° C.

Analysis for the formula $C_{28}H_{33}ClN_2O_6$ (535.09): Calculated: C %=62.85 H %=7.35 N %=5.24 Cl %=6.62 Found: C %=62.51 H %=7.45 N %=5.19 Cl %=6.66.

UV: $\lambda_{max}$=261 nm ($\epsilon$=19471).

EXAMPLE 45

Tablet comprising 25 mg of active ingredient a) The composition of one tablet is as follows:

| | |
|---|---|
| active ingredient | 25.0 mg |
| corn starch | 97.0 mg |
| polyvinyl-pyrrolidone | 175.0 mg |
| magnesium stearate | 3.0 mg |
| | 300.0 mg |

The tablet is prepared as follows:

The active ingredient and the corn starch are admixed, then wetted with 10 to 15% by weight of aqueous polyvinyl-pyrrolidone solution and the mixture is granulated then dried at a temperature of 40° to 50° C. The dry granules are rubbed through a sieve, mixed with stearate and tablets are prepared from the mixture.

The weight of one tablet is 300.0 mg.

b) The composition of one tablet is as follows:

| | |
|---|---|
| active ingredient | 25.0 mg |
| magnesium stearate | 0.5 mg |
| stearine | 0.5 mg |
| talc | 1.0 mg |
| gelatin | 1.7 mg |
| microcrystalline cellulose | 6.0 mg |
| corn starch | 15.3 mg |
| lactose | 50.0 mg |
| | 100.0 mg |

The tablet is prepared as follows:

The active ingredient, the corn starch, the lactose and the cellulose are admixed and granulated with 10% gelatin solution then dried at a temperature of 40° to 50° C. The dry granules are rubbed through a sieve, mixed with talc, stearine and magnesium stearate and tablets are prepared from the mixture.

The weight of one tablet is 100.0 mg.

EXAMPLE 46

Tablet comprising 250 mg of active ingredient
The composition of one tablet is as follows:

| | |
|---|---|
| active ingredient | 250.0 mg |
| lactose | 270.0 mg |
| corn starch | 75.0 mg |
| magnesium stearate | 5.0 mg |
| | 600.0 mg |

The acive ingredient, the lactose and the corn starch are wetted and mixed, granulated and dried at a temperature of 40° to 50° C. The dry granules are rubbed through a sieve as described hereinabove, mixed with magnesium stearate, then tablets are formed.

The weight of one tablet is 600.0 mg.

EXAMPLE 47

Dragée comprising 25 mg of active ingredient

The composition of one dragée core is as follows:

| | |
|---|---|
| active ingredient | 25.0 mg |
| corn starch | 245.0 mg |
| talc | 18.0 mg |
| gelatin | 8.0 mg |
| magnesium stearate | 4.0 mg |
| | 300.0 mg |

The active ingredient and the corn starch are mixed, wetted with 10% by weight aqueous gelatin solution, granules are formed from the wet mixture, then the granules are dried at a temperature of 40° to 50° C. The dry granules are rubbed through a sieve, homogenized with talc and magnesium stearate and dragée cores of 300.0 mg are compressed from the mixture.

EXAMPLE 48

Dragée comprising 50.0 mg of active ingredient

The composition of one dragée core is as follows:

| | |
|---|---|
| active ingredient | 50.0 mg |
| lactose | 97.0 mg |
| polyvinyl-pyrrolidone | 2.0 mg |
| magnesium stearate | 1.0 mg |
| | 150.0 mg |

The granules are prepared as described hereinabove. The weight of the dragée cores is 150 mg.

The dragée cores are coated with a layer containing sugar and talc in a manner known per se. The dragée thus obtained is painted with non-toxic food paint to the desired colour and polished with bee-wax.

EXAMPLE 49

Gelatin capsule comprising 5.0 mg of active ingredient

The composition of one gelatin capsule is as follows:

| | |
|---|---|
| active ingredient | 5.0 mg |
| corn starch | 40.0 mg |
| Aerosil | 3.0 mg |
| magnesium stearate | 2.0 mg |
| | 50.0 mg |

The ingredients are homogenized and filled into gelatin capsules of suitable size.

EXAMPLE 50

Gelatin capsule comprising 25.0 mg of active ingredient

The composition of one gelatin capsule is as follows:

| | |
|---|---|
| active ingredient | 25.0 mg |
| corn starch | 265.0 mg |
| Aerosil | 6.0 mg |
| magnesium stearate | 4.0 mg |
| | 300.0 mg |

The ingredients are homogenized and filled into gelatin capsules of suitable size.

EXAMPLE 51

Gelatin capsule comprising 50.0 mg of active ingredient

The composition of one gelatin capsule is as follows:

| | |
|---|---|
| active ingredient | 50.0 mg |
| lactose | 90.0 mg |
| Aerosil | 6.0 mg |
| magnesium stearate | 4.0 mg |
| | 150.0 mg |

The ingredients are homogenized and filled into gelatin capsules of suitable size.

EXAMPLE 52

Gelatin capsule comprising 250.0 mg of active ingredient

The composition of one gelatin capsule is as follows:

| | |
|---|---|
| active ingredient | 250.0 mg |
| lactose | 148.0 mg |
| magnesium stearate | 2.0 mg |
| | 400.0 mg |

The ingredients are homogenized and filled into gelatin capsules of suitable size.

EXAMPLE 53

Injection comprising 25.0 mg of active ingredient

The composition of one ampoule is as follows:

| | |
|---|---|
| active ingredient | 25.0 mg |
| sodium chloride | 5.0 mg |

The active ingredient and the sodium chloride are dissolved in the necessary amount of twice-distilled water suitable for making injections. The solution is filtered, filled into ampoules and sterilized.

EXAMPLE 54

Injection comprising 50.0 mg of active ingredient

The composition of one ampoule is as follows:

| | |
|---|---|
| active ingredient | 50.0 mg |
| sodium chloride | 10.0 mg |

The active ingredient and the sodium chloride are dissolved in the necessary amount of twice-distilled water, then filled into ampoules under sterile conditions.

EXAMPLE 55

Suppository comprising 250 mg of active ingredient

The composition of one suppository is as follows:

| active ingredient | 250.0 mg |
|---|---|
| fatty acid glyceride | 750.0 mg |

The fatty acid glyceride is melted, the active ingredient is homogenized, then poured into a mould. One suppository weights 1000.0 mg and comprises 250.0 mg of active ingredient.

EXAMPLE 56

Drop comprising 5% by weight of active ingredient
The composition of the drop-solution is as follows:

| active ingredient | 50.0 mg |
|---|---|
| sorbitol | 340.0 mg |
| polyethylene glycol | 100.0 mg |
| citric acid | 1.0 mg |
| sodium citrate | 3.0 mg |
| ion-free water | 505.0 mg |
| flavourant | 1.0 mg |
| | 1000.0 mg |

The sorbitol, the active ingredient, citric acid and sodium citrate are dissolved in the aqueous solution of propylene glycol, then after dissolution of the solid materials the flavourant is added. The solution is filtered and filled into flasks supplied with a drop-dispenser.

What we claim is:

1. A trisubstituted cycloalkane compound selected from the group consisting of (R,S)-6-(E)-(4-fluorophenylmethylene)-2-pentyl-1-(E)-[2-(4-phenylmethyl-1-piperazinyl)-ethoxyimino]-cyclohexane, (R,S)-2-propyl-7-(E)-(4-chlorophenylmethylene)-1-(E)-[2-hydroxy-3-(N-pyrrolidinylpropoxyimino)]-cycloheptane, (R,S)-6-(E)-(4-fluorophenylmethylene)-2-methyl-1-(E)-[3-(dimethylamino)-2-methylpropoxyimino)-cyclohexane, (R,S)-6-(E)-(2-methoxyphenylmethylene)-2-hexyl-1-(E)-[2-(diethylamino)-ethoxyimino]-cyclohexane, (R,S)-6-(E)-(4-fluorophenylmethylene)-2-heptyl-1-(E)-[2-dimethylamino)-ethoxyimino]-cyclohexane, and (R,S)-7-(E)-(chlorophenylmethylene)-2-propyl-1-(E)-[2-(diethylamino)-ethoxyimino]-cycloheptane, its stereo and optically active isomer or racemic mixture, its acid-addition salt or quaternary ammonium salt.

2. A pharmaceutical composition comprising as active ingredient at least one cycloalkane according to claim 1 or a pharmaceutically acceptable acid-addition salt and/or quaternary ammonium salt thereof in admixture with suitable inert solid or liquid pharmaceutical carriers.

3. A method of ulcer and gastric-acid-secretion inhibiting treatment, which comprises administering to a patient an effective amount of at least one cycloalkane according to claim 1 or a pharmaceutically acceptable acid-addition salt or quaternary ammonium salt thereof.

4. A method of cytoprotection of the stomach, said method comprising administering to a patient an effective amount of at least one cycloalkane according to claim 1 or a pharmaceutically acceptable acid-addition salt or quaternary ammonium salt thereof.

* * * * *